United States Patent [19]
Lindsey

[11] Patent Number: 5,589,605
[45] Date of Patent: Dec. 31, 1996

[54] HYBRID CORN WITH A GENETIC COMPLEMENT PRODUCING INCREASED YIELD, SEEDLING VIGOR, EARLY STAND, STALK STRENGTH AND LOW HARVEST MOISTURE

[75] Inventor: Marvin F. Lindsey, Boone, Iowa

[73] Assignee: DeKalb Genetics Corporation, DeKalb, Ill.

[21] Appl. No.: 610,460

[22] Filed: Nov. 8, 1990

Related U.S. Application Data

[63] Continuation of Ser. No. 463,848, Jan. 12, 1990, abandoned, which is a continuation of Ser. No. 187,188, Apr. 28, 1988, abandoned.

[51] Int. Cl.$^6$ .............................. A01H 5/00; A01H 1/00
[52] U.S. Cl. .................. 800/200; 800/250; 800/DIG. 56; 47/58; 47/DIG. 1
[58] Field of Search ...................................... 800/200, 250, 800/DIG. 56; 47/58

[56] References Cited

U.S. PATENT DOCUMENTS 4,654,466  3/1987  Lindsey ...................................... 800/200

OTHER PUBLICATIONS

Allard (1960) Principles of Plant Breeding pp. 67–69.

Phillips et al. (1988) Cell & Tissue Culture In Vitro Manipulation in Corn & Corn Improvement ASA Publishers #18, 3rd Edition.

Poehlman (1986) *Breeding Field Crops* 3rd Ed. AVI publishing company, Westport, CT pp. 469–471 & 477–481.

Sprague et al. (1977) In/corn and Corn Improvment Ed. G. F. Sprague. ASA Inc. Publisher #18, Madison WI pp. 305, 320–323.

Green et al. (1982) In/Maize for Biological Research Ed. W. Sheridan U. Press N. Dakota, pp. 367–372.

*Primary Examiner*—Gary Benzion
*Attorney, Agent, or Firm*—Arnold, White & Durkee

[57] ABSTRACT

$F_1$ hybrid corn plant EXP 748, seeds produced by cultivation of the hybrid, and plant cells which upon growth and differentiation produce the hybrid, are disclosed. Also disclosed are processes for production of the corn plants.

2 Claims, No Drawings

5,589,605

HYBRID CORN WITH A GENETIC COMPLEMENT PRODUCING INCREASED YIELD, SEEDLING VIGOR, EARLY STAND, STALK STRENGTH AND LOW HARVEST MOISTURE

This application is a continuation of application Ser. No. 07/463,848, filed Jan. 12, 1990, now abandoned, which was a continuation of application Ser. No. 07/187,188, filed Apr. 28, 1988, and now abandoned.

BACKGROUND OF THE INVENTION

This invention relates generally to the production of maize, commonly known in the United States as corn, and more particularly concerns the development and production of inbred and hybrid maize with certain desired characteristics.

Commercial hybrid maize generally grows from about 7 to 9 feet tall with each plant having either one or two ears. The ear normally grows about one-third the way up the plant or about 2½ to 3½ feet from the ground. Consequently, the maize plant, while providing a large ear, has a substantial leaf and stalk structure and a considerable mechanical stability problem in that the heavy ear is about 3 feet from the ground with 6 feet of stalk and the tassels extend above the stalk above that. In the past, efforts have been made to develop strong stalk and branching of secondary roots in maize to help alleviate this stability problem. While these efforts have improved the mechanical stability of maize considerably, heavy wind storms and rain can still wreak havoc in a field of maize.

While great gains have been made in the use of hybrid maize in productivity and yield per acre, over that of open-pollinated maize varieties, further major and immediate substantial gains are always desirable. Consequently, efforts must be directed to improving the characteristics of the commercial hybrid maize plant by genetic or environmental manipulation.

Hence, one of the objects of this invention is to significantly increase the yield per acre of maize. For example, in the Apr. 17, 1974 edition of *The Wall Street Journal*, the article entitled, "In Search of Superbean," it was pointed out that soybeans could not easily be hybridized and, therefore, fell far behind corn in productivity increase. During the period of 1950 to 1973, soybeans increased in productivity from 21.8 to 27.8 bushels per acre while corn increased from 38.4 to 91.4 bushels per acre.

Other advantageous characteristics can also be sought by the methods of plant breeding and genetic manipulation. For example, excellent plant seedling vigor is advantageous as are early stand, stalk strength and low harvest moisture characteristics. The present invention provides a novel corn hybrid with all of these advantages and other advantageous characteristics as well.

SUMMARY OF THE INVENTION

The present invention comprises novel $F_1$ generation hybrid corn plants designated EXP 748. Seeds of this hybrid have been deposited with American Type Culture Collection, 12301 Parklawn Drive, Rockville, Md. 20852 and have received accession number ATCC 40470. The invention further comprises novel hybrid corn seed EXP 748 and the novel seeds produced by the cultivation of novel hybrid EXP 748 corn plant. Cells, or tissue, which upon growth and differentiation produce novel hybrid corn plants EXP 748 also form a part of this invention.

The present invention is also directed to a process for producing an $F_1$ generation hybrid corn plant comprising (a) planting in pollinating proximity seeds of corn varieties wherein the male parent is 78551S and the female parent is 78010;

(b) cultivating corn plants resulting from said planting until time of flowering;

(c) at said flowering time, emasculating said flower of said plants of said female parent 78010;

(d) allowing natural cross pollination to occur between said varieties and;

(e) harvesting seeds produced on said plants of the female parent 78010.

DETAILED DESCRIPTION OF THE INVENTION

As the female parent used to produce the novel hybrid corn plants and seeds of the present invention, a proprietary inbred line 78010 developed by DeKalb Pfizer Genetics was employed. A proprietary inbred line 78551S, also developed by DeKalb Pfizer Genetics, was used as the male parent.

The two parental inbred lines, 78010 and 78551S, were planted in pollinating proximity to each other in alternating rows. They also can be planted in blocks or in any convenient planting pattern that allows for free transfer of pollen. The plants of both varieties were allowed to grow unmolested until time of flowering with one application of fertilizer, if desired, being applied at the seedling stage. They can be thinned at about the 3-leaf stage if desired, and also can be treated with other agricultural chemicals as considered appropriate by the seed grower. At the time of flowering, the tasksels were removed from all plants of the female parent 78010. This was accomplished by hand but can be done by machine as desired, or without detasseling by use of females that carry one of several well known male sterility traits, most commonly conferred by a cytoplasmic genome. Both varieties were then allowed to continue to grow and natural cross-pollination occurred by the action of wind as is normal in grasses, including corn. Of course only pollen from the male parent variety, 78551S, was available for pollination, the tassels, or pollen bearing flowering parts, having been removed from all plants of the female variety. In this regard, the fields where the hybrid seeds of this invention were produced were well isolated from other corn fields to prevent any accidental contamination with ambient pollen. Such isolation techniques are normal in the seed corn industry and are well known to those skilled in the art.

Both parent varieties of corn were allowed to continue to grow but the ears from the female parent variety only were harvested to obtain the novel $F_1$ hybrid corn seeds, EXP 748, of the present invention. The male parent variety ears will not be useful as hybrid seed corn.

To obtain the novel $F_1$ hybrid corn plants of the present invention, the seeds thus produced were planted at the next proper growing season. All parts of such plants of hybrid EXP 748 are claimed as a part of the present invention including roots, stems, leaves and all flowering parts, including pollen grains. The cells of plants of hybrid EXP 748 which can be grown in culture and differentiated or regenerated to form hybrid plants also constitute a part of this invention. For details of regeneration procedures, see C. E. Green and C. A. Rhodes, "Plant Regeneration In Tissue Culture of Maize," 1982, *Maize for Biological Research*, ed.

W. F. Sheridan, Plant Molecular Biology Association, Charlottesville, Va. p. 367–372.

Furthermore, the seeds produced by $F_1$ hybrid EXP 748 plants on maturity also form a part of the present invention. The novel $F_1$ hybrid corn seeds, EXP 748, were planted and the resulting hybrid plants were grown to maturity, the ears being harvested mechanically by normal means.

The Tables to follow compare the characteristics of EXP 748 to other leading commercial hybrids.

TABLE 1

Comparison of EXP 748 With Other Hybrids

| Hybrid | Yield (Bushels/acre) | Harvest Moisture (%) | Seedling Vigor (%) | Early Stand (%) | Plant Height (inches) | Ear Height (inches) | Barren (%) | Stay Green (%) | Stalk Lodged (%) | Root Lodged (%) |
|---|---|---|---|---|---|---|---|---|---|---|
| EXP 748 | 135.7 | 19.5 | 4.9 | 92.2 | 85.0 | 38.4 | 0.5 | 3.5 | 1.8 | 0.4 |
| DK 484 | 127.1 ** | 19.8 | 5.5 ** | 102.7 ** | 83.6 ** | 39.5 ** | 0.7 | 3.6 ** | 2.9 | 1.0 |
| EXP 748 | 145.2 | 20.3 | 4.7 | 89.1 | 85.1 | 39.6 | 0.3 | 4.9 | 4.6 | 3.2 |
| PION 3737 | 135.5 ** | 18.4 ** | 5.8 ** | 103.4 ** | 83.5 ** | 39.1 | 0.5 * | 4.7 | 7.5 ** | 3.1 * |

** statistically significant at the 1% level
* statistically significant at the 5% level
+ statistically significant at the 10% level Table 2: General Characteristics of EXP 748.

| | |
|---|---|
| Days from Emergence to 50% silk | 73 |
| Plant Height (cm) from ground | 270 |
| Ear Height (cm) from ground | 124 |
| Ear Length (cm) | 17 |
| Tillers/Plant | 0 |
| No. of Ears/Stalk | 1.0 |
| Leaf Color | Medium Green |
| Leaf Angle | Upright |
| Leaf Sheath Pubescence | Light |
| Leaves/Plant | 20 |
| Tassel Branch Number | 7 |
| Tassel Branch Angle | Intermediate |
| Anther Color | Yellow |
| Silk Color | Medium Green |

-continued

| | |
|---|---|
| Disease Reaction; S = Susceptible, R = Resistant | |
| Anthracnose (foliar phase) | R |
| Eyespot | R |
| Goss's Disease | R |

What is claimed is:

1. $F_1$ generation hybrid corn plant EXP 748, wherein a sample of seed of EXP 748 has been deposited under ATCC accession No. 40470.

2. Seed produced by the cultivation of the hybrid corn plant of claim 1.

* * * * *